(12) United States Patent
Boll et al.

(10) Patent No.: US 7,863,260 B2
(45) Date of Patent: Jan. 4, 2011

(54) HYDROXYETHYLSTARCH

(75) Inventors: Michael Boll, Melsungen (DE); Andreas Fisch, Lausanne (CH); Donat R. Spahn, Zurich (CH)

(73) Assignee: B. Braun Melsungen AG, Melsungen (DE)

( * ) Notice: Subject to any disclaimer, the term of this patent is extended or adjusted under 35 U.S.C. 154(b) by 769 days.

(21) Appl. No.: 10/590,462

(22) PCT Filed: Mar. 1, 2005

(86) PCT No.: PCT/EP2005/050877

§ 371 (c)(1), (2), (4) Date: Jul. 30, 2007

(87) PCT Pub. No.: WO2005/082942

PCT Pub. Date: Sep. 9, 2005

(65) Prior Publication Data

US 2007/0282014 A1 Dec. 6, 2007

(30) Foreign Application Priority Data

Mar. 1, 2004 (EP) ................................. 04100813

(51) Int. Cl.
*A61K 31/718* (2006.01)
*C08B 33/04* (2006.01)
*C08B 35/04* (2006.01)

(52) U.S. Cl. ..................... 514/60; 536/111; 536/123.12

(58) Field of Classification Search ....................... None
See application file for complete search history.

(56) References Cited

U.S. PATENT DOCUMENTS

| | | | | |
|---|---|---|---|---|
| 4,775,638 A | * | 10/1988 | Haisma | ...................... 424/1.49 |
| 5,218,108 A | * | 6/1993 | Sommermeyer et al. | .... 536/111 |
| 5,502,043 A | | 3/1996 | Weidler et al. | |
| 6,083,909 A | * | 7/2000 | Sommermeyer et al. | ....... 514/6 |
| 6,610,294 B1 | * | 8/2003 | Lederman et al. | ........ 424/154.1 |
| 6,680,305 B1 | | 1/2004 | Segall et al. | |
| 7,285,661 B2 | * | 10/2007 | Sommermeyer et al. | ...... 536/45 |

FOREIGN PATENT DOCUMENTS

| | | | |
|---|---|---|---|
| EP | 0170275 A1 | | 2/1986 |
| EP | 0402724 A1 | | 12/1990 |
| GB | 1395777 | | 5/1975 |
| WO | WO 00/48637 | | 8/2000 |
| WO | WO03/070772 | * | 8/2003 |

OTHER PUBLICATIONS

"STN Database Descriptions" from 2006 Chemical Abstracts Catalog, published 2006 by Chemical Abstracts Service, p. 52.*
Felfenig et al., "The effects of hydroxyethyl starch solutions on thromboelastography in preoperative male patients" Acta Anaesthesiol Scand (2003) vol. 47 pp. 70-73.*
Deusch, "The Effects of High Molecular Weight Hydroxyethyl Starch Solutions on Platelets" Anesthesia and Analgesia (2004) vol. 99, pp. 665-668.*
Jaeger et al., "Effects of colloidal resuscitation fluids on the neutrophil respiratory burst" Transfusion (2001) vol. 41 pp. 1064-1068.*
Madjpour et al., "Molecular weight of hydroxyethyl starch: is there an effect on blood coagulation and pharmacokinetics?" British Journal of Anaesthesia (2005) vol. 94 No. 5, pp. 569-576.*
De Belder, et al. "The Substitution Patterns of 0-(2-Hydroxyethyl)Starch and 0-(2-Hydroxyethyl)Dextran" Carbohydrate Research, XP002329873 Amsterdam das ganze Dokument, vol. 10, 1969, pp. 391-394.

* cited by examiner

*Primary Examiner*—Eric S Olson
(74) *Attorney, Agent, or Firm*—Klein, O'Neill & Singh, LLP

(57) ABSTRACT

Described are a hydroxyethylstarch, a process for the preparation thereof, a pharmaceutical formulation containing such a hydroxyethylstarch, and the use of the pharmaceutical formulation for the preparation of a volume replacement, a plasma replacement or a plasma volume expander, as well as the use of the pharmaceutical formulation for maintaining normovolemia and/or for improving the macro- and microcirculation and/or for improving the nutritive oxygen supply and/or for stabilizing hemodynamics and/or for improving the volume efficiency and/or for reducing the plasma viscosity and/or for increasing anemia tolerance and/or for hemodilution, especially for therapeutic hemodilution in disturbed blood supply and arterial, especially peripheral arterial, occlusive diseases.

52 Claims, 1 Drawing Sheet

HYDROXYETHYLSTARCH

CROSS-REFERENCE TO RELATED APPLICATIONS

This is a US national phase application of PCT/EP2005/050877, filed Mar. 1, 2005, which claims priority to a German Registration No. 04100813.7, filed Mar. 1, 2004, the contents of each of which are expressly incorporated herein by reference.

The invention relates to a hydroxyethylstarch, and to a process for the preparation of such a hydroxyethylstarch. Further, the invention relates to a pharmaceutical formulation containing a hydroxyethylstarch, and to the use of such a pharmaceutical formulation for the preparation of a volume replacement, a plasma replacement or a plasma expander, as well as to the use of the pharmaceutical formulation for maintaining normovolemia and/or for improving the macro- and microcirculation and/or for improving the nutritive oxygen supply and/or for stabilizing hemodynamics and/or for improving the volume efficiency and/or for reducing the plasma viscosity and/or for increasing anemia tolerance and/or for hemodilution, especially for therapeutic hemodilution in disturbed blood supply and arterial, especially peripheral arterial, occlusive diseases.

BACKGROUND

The use of intravascular fluid is among the most important measures in the prophylaxis and therapy of hypovolemia, irrespective of whether the hypovolemia results from the immediate loss of blood or body fluids (in acute bleedings, traumas, surgery, burns), from disturbed distribution between macro- and microcirculation (such as in sepsis), or from vasodilation (e.g., during the initiation of anesthesia). Infusions suitable for such indications are supposed to restore normovolemia and maintain the perfusion of vital organs and the peripheral blood flow. At the same time, the solutions must not stress the circulation excessively, and they must be possibly free from side effects. In this respect, all the currently available volume replacements have benefits and drawbacks. Although so-called crystalloid solutions (electrolyte solutions) are essentially free from immediate side effects, they ensure only a short-term or inadequate stabilization of the intravascular volume and the hemodynamics. In case of pronounced or persisting hypovolemia, they must be infused in excessive amounts because they do not exclusively remain in the intravascular compartment but quickly dissipate in the extravascular space. However, a fast flow-out into the extravascular space not only limits the circulation-filling effect of crystalloid solutions but also involves the risk of peripheral and pulmonary edemas. Apart from the vital threat which a lung edema can represent, it additionally leads to a deterioration of the nutritive oxygen supply, which is also affected by peripheral edemas.

In contrast, colloidal volume replacements, whether the colloids contained therein are of natural or synthetic origin, have a much more reliable effect. This is due to the fact that, because of their colloid-osmotic effect, they retain the supplied liquid longer in the circulation as compared to crystalloids and thus protect them from flowing out into the interstice. On the other hand, colloidal volume replacements cause a higher extent of undesirable responses as compared to crystalloid solutions. Thus, the natural colloid albumin, like all blood or plasma derivatives, involves the risk of infection with viral diseases; in addition, it may result in interactions with other drugs, e.g., ACE inhibitors; finally, the availability of albumin is limited, and its use as a volume replacement is disproportionately expensive. Further doubts as to the use of albumin as a volume replacement are due to the inhibition of the endogenous synthesis of albumin if it is added exogenously and due to its ready extravascularization. This means the passage from the circulation into the extravascular space, where undesirable and persistent liquid accumulations can occur because of the colloid-osmotic effect of albumin.

In the synthetic colloids, severe anaphylactoid responses and a massive inhibition of blood coagulation have caused dextran preparations to disappear almost completely from therapy. Although hydroxyethylstarch (HES) solutions also have the potential for triggering anaphylactoid responses and affecting blood coagulation, this is to a lesser extent as compared with dextran. Severe anaphylactoid responses (responses of severity III and IV) are observed extremely rarely with HES solutions, in contrast to dextran, and the influence on blood coagulation, inherent to the high-molecular weight HES solutions, could be significantly reduced in recent years by the further development of HES solutions. As compared with gelatin solutions, which also find use as plasma replacements and leave blood coagulation essentially unaffected, HES solutions, at least their high- and medium-molecular weight embodiments, have the benefit of a longer plasma residence time and effectiveness.

EP-A-0 402 724 discloses the preparation and use of a hydroxyethylstarch having an average molecular weight, Mw, of from 60,000 to 600,000, a molar substitution, MS, of from 0.15 to 0.5, and a degree of substitution, DS, of from 0.15 to 0.5. The disclosure deals with the rapid (6 to 12 hours) and complete degradability of the hydroxyethylstarches to be employed as plasma expanders. Within the preferred range of average molecular weights of from 100,000 to 300,000, a hydroxyethylstarch having an average molecular weight of 234,000 was explicitly examined.

U.S. Pat. No. 5,502,043 discloses the use of hydroxyethylstarches having an average molecular weight, Mw, of from 110,000 to 150,000, a molar substitution, MS, of from 0.38 to 0.5, and a degree of substitution, DS, of from 0.32 to 0.45 for improving microcirculation in peripheral arterial occlusive disease. In addition, the document teaches the use of low-molecular weight (Mw 110,000 to 150,000) hydroxyethylstarches which, due to their low molecular weight, keep the plasma viscosity low and thus ensure an improvement of microcirculation in the blood flow. However, this document advises against the use of higher-molecular weight hydroxyethylstarches, such as a hydroxyethylstarch with an Mw of 500,000, because they increase plasma viscosity and thus deteriorate microcirculation despite their low molar substitution (MS=0.28).

Worldwide, different HES preparations are currently used as colloidal volume replacements, which are mainly distinguished by their molecular weights and additionally by their extent of etherification with hydroxyethyl groups, and by other parameters. The best known representatives of this class of substances are the so-called Hetastarch (HES 450/0.7) and Pentastarch (HES 200/0.5). The latter is the currently most widespread "standard HES". Besides, HES 200/0.62 and HES 70/0.5 play a minor role. The declared information relating to the molecular weight as well as that relating to the other parameters are averaged quantities, where the molecular weight declaration is based on the weight average (Mw) expressed in Daltons (e.g., for HES 200,000) or mostly abbreviated in Kilodaltons (e.g., for HES 200). The extent of etherification with hydroxyethyl groups is characterized by the molar substitution MS (e.g. as 0.5 such as in HES 200/0.5; MS=average molar ratio of hydroxyethyl groups to anhydroglucose units) or by the degree of substitution (DS=ratio of mono- or polyhydroxyethylated glucoses to the total anhydroglucose units). According to their molecular weights, the HES solutions in clinical use are classified into high-molecular weight (450 kD), medium-molecular weight (200-250 kD) and low-molecular weight (70-130 kD) preparations.

As to the coagulation effects of HES solutions, a distinction is to be made between non-specific and specific influences. A non-specific influence on blood coagulation results from dilution of the blood (hemodilution), which occurs during the infusion of HES solutions and other volume replacements into the circulation. Affected by this hemodilution are also coagulation factors, whose concentrations are decreased depending on the extent and duration of the dilution of the blood and the plasma proteins due to the infusion. Correspondingly large or persisting effects may result in a hypocoagulability which is detectable by laboratory diagnostics and, in extreme cases, clinically relevant.

In addition, hydroxyethylstarch may cause a specific influence on blood coagulation, for which several factors are held responsible. Thus, under certain conditions or with certain HES preparations, a decrease of the coagulation proteins factor VIII (F VIII) and von Willebrand factor (vWF) is found which is larger than the general decrease of the plasma proteins due to hemodilution. Whether this larger than expected decrease is caused by a reduced formation or release of F VIII/vWF, such as by coating effects on the vascular endothelium caused by HES, or by other mechanisms is not quite clear.

However, HES influences not only the concentration of the coagulation factors mentioned but evidently also the function of platelets. This is completely or in part due to the binding of HES to the surface of the platelets, which inhibits the access of ligands to the fibrinogen receptor of the platelets.

These specific effects of HES on blood coagulation are particularly pronounced when high-molecular weight HES (e.g., HES 450/0.7) are employed while they do not play such a great role for medium-molecular weight (e.g., HES 250/0.5) or low-molecular weight HES (e.g., HES 130/0.4 or HES 70/0.5) (J. Treib et al., Intensive Care Med. (1999), pp. 258 to 268; O. Langeron et al., Anesth. Analg. (2001), pp. 855 to 862; R. G. Strauss et al., Transfusion (1988), pp. 257-260; M. Jamnicki et al., Anesthesiology (2000), pp. 1231 to 1237).

If the risk profile of high-molecular weight HES is compared with that of the medium- and low-molecular weight preparations, a clear reduction of the risks can be established in the latter, i.e., not only with respect to the interaction with blood coagulation but also with respect to particular pharmacokinetic properties. Thus, the high-molecular weight HES solutions show a high accumulation in the circulation while this drawback is reduced in medium-molecular weight HES and virtually absent in low-molecular weight preparations. The fact that no more accumulation occurs with low-molecular weight HES solutions, such as HES 130/0.4, is a relevant therapeutic progress because the plasma levels of HES cannot be determined in clinical routine, and therefore, even extreme concentrations, which can be obtained within a few days with the high-molecular weight solutions, remain undiscovered. In this case, the amount of "residual HES" accumulated in the circulation is unknown to the user but it nevertheless influences the kinetics and behavior of the HES which was additively infused, not knowing the amounts still present in the circulation. Therefore, the effect of high-molecular weight HES according to the prior art is not calculable; it remains longer in the circulation than would be required or desired for therapeutic reasons in most cases, and its metabolic fate is unclear.

In contrast, low-molecular weight HES will disappear completely from the circulation within about 20 to 24 hours after the infusion. This avoids backlog effects, and no accumulation occurs, especially for repeated infusions. The pharmacokinetic behavior of low-molecular weight starch, in contrast to high-molecular weight starch, is calculable and therefore can be easily controlled. Too high a load on the circulation or the clearance mechanisms does not occur.

However, this behavior of low-molecular weight HES as compared to high-molecular weight preparations, which is advantageous as such, is purchased at the expense of a significantly shorter plasma half life. The plasma half life of low-molecular weight HES is only about half that of HES 200 or less (J. Waitzinger et al., Clin. Drug Invest. (1998), pp. 151 to 160) and is in the range of the half life of gelatin preparations, which are to be rated as decidedly short-term effective. Although a short half life of a volume replacement need not be categorically disadvantageous, because it can be compensated for by a more frequent or more highly dosed administration of the volume replacement in question, in severe or persisting hypovolemia, a volume replacement with a short half life and short effective period involves the risk of insufficient circulation filling (much like with crystalloid solutions) or, when the dosage is correspondingly increased for compensating for this drawback, the risk of interstitial liquid overload.

DETAILED DESCRIPTION

Figure 1:
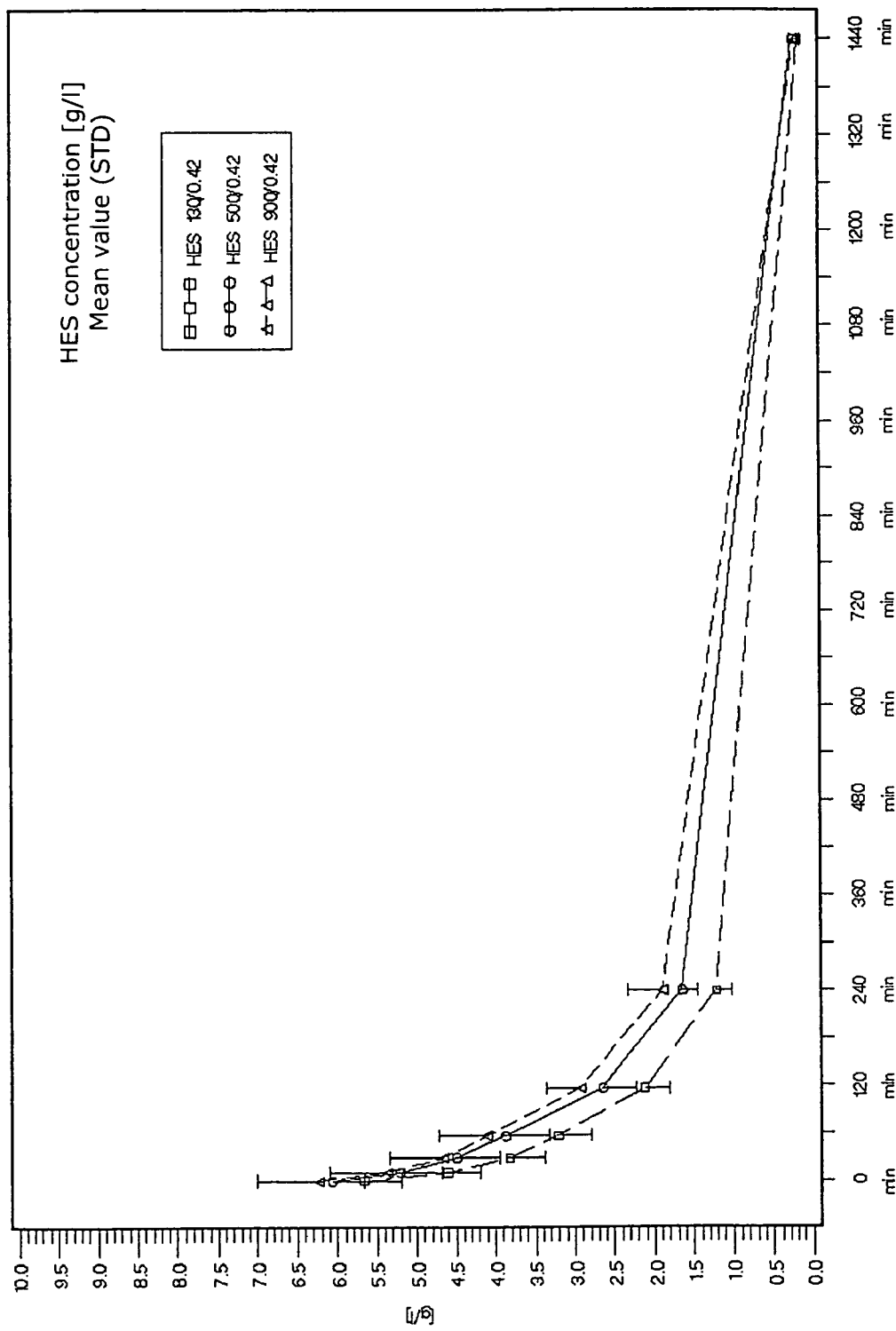
FIG. 1 shows the course of the concentration of low-molecular weight HES and high-molecular weight HES in the plasma after infusion over time.

Before this background, there is a need for a volume replacement which on the one hand is characterized by a low tendency to accumulation and a low influence on blood coagulation (such as low-molecular weight HES) but on the other hand has a longer half life as compared to the low-molecular weight HES solutions, whose properties are close to those of crystalloid solutions.

Searching for a hydroxyethylstarch having such properties, it has now been found that there very well is a hydroxyethylstarch for HES solutions with longer plasma half lives as compared to known low-molecular weight HES solutions, and that these can also be prepared and, surprisingly, without these high-molecular weight solutions according to the invention having the drawbacks of previous high-molecular weight solutions, such as their property to become accumulated in the circulation or their pronounced inhibition of blood coagulation.

Therefore, in one embodiment, the invention relates to a hydroxyethylstarch having an average molecular weight, Mw, of greater than or equal to 500,000, the molar substitution MS being from 0.25 to 0.5, preferably from 0.35 to 0.50 ($0.35 \leq MS \leq 0.50$), and the $C_2/C_6$ ratio being from 2 to below 8.

The hydroxyethylstarches according to the invention are influenced by the molar substitution MS. The molar substitution MS is defined as the average number of hydroxyethyl groups per anhydroglucose unit (Sommermeyer et al., Krankenhauspharmazie (1987), pp. 271 to 278). The molar substitution can be determined according to Ying-Che Lee et al., Anal. Chem. (1983) 55, 334, and K. L. Hodges et al., Anal. Chem. (1979) 51, 2171. In this method, a known amount of HES is subjected to ether cleavage by adding adipic acid and hydroiodic acid (HI) in xylene. Subsequently, the ethyl iodide released is quantified by gas chromatography using an internal standard (toluene) and external standards (ethyl iodide calibrating solutions). The molar substitution MS influences the effect of the hydroxyethylstarches according to the invention. If the MS is selected too high, this may cause an accumulation effect in the circulation when the hydroxyethylstarches are employed as a volume replacement. On the other hand, if the MS is selected too low, this may result in too rapid a degradation of the hydroxyethylstarch in the circulation and thus reduce the desired duration of the plasma half life. A molar substitution MS of from 0.35 to 0.5 ($0.35 \leq MS \leq 0.50$), preferably from 0.39 to smaller than or equal to 0.45 ($0.39 \leq MS \leq 0.45$) and especially an MS of from greater than 0.4 to 0.44 ($0.4 < MS \leq 0.44$), has proven advantageous.

The hydroxyethylstarches according to the invention belong to the higher-molecular weight hydroxyethylstarches and preferably have an average molecular weight (Mw) of above 600,000 to 1,500,000, more preferably from 620,000 to 1,200,000, especially from 700,000 to 1,000,000. Due to the preparation conditions, the hydroxyethylstarches are not in the form of a substance with a defined uniform molecular weight but in the form of a mixture of molecules of different sizes which are also differently substituted by hydroxyethyl groups. Therefore, the characterization of such mixtures requires recourse to statistically averaged quantities. Therefore, the weight-average molecular weight (Mw) serves for characterizing the average molecular weight, the general definition of this mean value being stated in Sommermeyer et al., Krankenhauspharmazie (1987), pp. 271 to 278.

The molecular weight determination can be effected by means of GPC-MALLS using the GPC columns TSKgel G 6000 PW, G 5000 PW, G 3000 PW and G 2000 PW (7.5 mm×30 cm), the MALLS detector (DAWN-EOS; Wyatt Deutschland GmbH, Woldert) and the RI detector (Optilab DSP; Wyatt Deutschland GmbH, Woldert) at a flow rate of 1.0 ml/minute in a 50 mM phosphate buffer, pH 7.0. The evaluation may be performed by means of ASTRA software (Wyatt Deutschland GmbH, Woldert).

Preferred are those hydroxyethylstarches which are obtainable from native or partially hydrolyzed cereal or potato starches. Due to their high content of amylopectin, the use of starches from waxy varieties of the corresponding crops, if they exist (e.g., waxy maize, waxy rice), is particularly advantageous.

The hydroxyethylstarch according to the invention is further described by the ratio of substitution at $C_2$ to substitution at $C_6$ of the anhydroglucose units. This ratio, which is also abbreviated as $C_2/C_6$ ratio within the scope of this invention, means the ratio of the number of anhydroglucose units substituted in 2 position to the number of anhydroglucose units substituted in 6 position of the hydroxyethylstarch. The $C_2/C_6$ ratio of an HES can be varied widely by the amount of aqueous sodium hydroxide used in the hydroxyethylation, as shown in Tables 1 and 2. The higher the amount of NaOH employed, the more highly the hydroxy groups in 6 position in the anhydroglucose of the starch are activated for hydroxyethylation. Therefore, the $C_2/C_6$ ratio decreases during the hydroxyethylation with increasing NaOH concentration. The determination is effected as stated by Sommermeyer et al., Krankenhauspharmazie (1987), pp. 271 to 278. With increasing preference in the order given, the $C_2/C_6$ ratios are preferably from 3 to below 8, from 2 to 7, from 3 to 7, from 2.5 to smaller than or equal to 7, from 2.5 to 6, or from 4 to 6. In the higher-molecular weight HES according to the invention, the $C_2/C_6$ ratio is another contribution to achieving the objects of the invention.

Due to their excellent tolerability and ready degradability in the human or animal organism, the hydroxyethylstarches according to the invention are suitable for being employed in a wide variety of pharmaceutical formulations.

In a particular embodiment, the HES according to the invention have an average molecular weight of from 700,000 to 1,000,000, a molar substitution of from above 0.4 to 0.44 ($0.4 < MS \leq 0.44$), and a $C_2/C_6$ ratio of from 2 to 7, preferably from 3 to 7, and especially from 2.5 to 6.

The present invention further relates to a process for the preparation of hydroxyethylstarch, preferably a hydroxyethylstarch according to the invention. Preferably, the process comprises the following steps:

(i) reacting water-suspended starch, preferably corn starch, more preferably partially hydrolyzed, so-called thin boiling, waxy maize starch, with ethylene oxide; and (ii) partially hydrolyzing the starch derivative obtained with acid, preferably hydrochloric acid, until the desired range of average molecular weight of the hydroxyethylstarch has been reached.

In principle, all known starches are suitable for the preparation of the hydroxyethylstarches according to the invention, mainly native or partially hydrolyzed starches, preferably cereal or potato starches, especially those having a high content of amylopectin. In a particular embodiment of the process according to the invention, starches from waxy varieties, especially waxy maize and/or waxy rice, are employed. In a particular embodiment, the preparation of HES is effected by reacting water-suspended cereal and/or potato starch, preferably thin boiling waxy maize starch, with ethylene oxide. Advantageously, the reaction is catalyzed by adding alkalizing agents, preferably alkali metal hydroxides, for example, sodium hydroxide or potassium hydroxide. Therefore, in a preferred embodiment of the process according to the invention, an alkalizing agent, preferably sodium hydroxide, is additionally added to the water-suspended starch. The alkalizing agent is added to the suspended starch preferably in such an amount that the molar ratio of alkalizing agent to starch is greater than 0.2, preferably from 0.25 to 1, especially from 0.3 to 0.8. Through the ratio of ethylene oxide to starch during the hydroxyethylation step, the molar substitution, i.e., the molar ratio of hydroxyethyl groups to anhydroglucose units, can be arbitrarily controlled over the desired MS range. Preferably, the reaction between ethylene oxide and suspended starch is effected in a temperature range of from 30 to 70° C., preferably from 35 to 45° C. Usually, any residues of ethylene oxide are removed after the reaction. In a second step following the reaction, an acidic partial hydrolysis of the derivatized starch is effected. "Partial hydrolysis" means the hydrolysis of the alpha-glycosidically interconnected glucose units of the starch. In principle, all acids familiar to the skilled person can be employed for the acidic hydrolysis, but preferred are mineral acids, especially hydrochloric acid. The hydrolysis may also be effected enzymatically using commercially available amylases.

In another preferred embodiment, the process according to the invention additionally comprises the steps of (iii) sterile filtration and optionally (iv) ultrafiltration. If the above described filtrations are performed in the process according to the invention, the acidic partial hydrolysis of the raw HES is effected to an average molecular weight which is slightly below the desired target molecular weight. By ultrafiltration, low-molecular weight reaction by-products, mainly ethylene glycol, can be removed, the average molecular weight slightly increasing due to the elimination of part of the low-molecular weight HES fraction.

Preferably, the solutions derived from the preparation process are subsequently diluted to the desired HES concentration, adjusted to the desired osmotic pressure by adding salt, subjected to sterile filtration and filled into suitable containers. Optionally, sterilization, preferably by live steam, can be effected.

Therefore, the present invention further relates to a pharmaceutical formulation containing one or more hydroxyethylstarches according to the invention. In principle, the pharmaceutical formulation according to the invention can be provided in any possible galenic dosage form. In a preferred embodiment of the present invention, the pharmaceutical formulations according to the invention can be injected or infused intravenously. Therefore, the pharmaceutical formulations are preferably in the form of an aqueous solution or colloidal aqueous solution. Preferably, the formulations contain the hydroxyethylstarches according to the invention in a concentration of up to 20%, more preferably from 0.5 to 15%, more preferably from 2 to 12%, especially from 4 to 10%, for example, 6%.

Unless stated otherwise, the amounts are expressed in %, which is to be understood as meaning g/100 ml of solution within the scope of the present invention.

In a further embodiment, the pharmaceutical formulations according to the invention additionally contain sodium chloride, preferably from 0.6 to 2%, more preferably 0.9%. A 0.9% solution of sodium chloride in water is also referred to as "physiological saline". It has the same osmotic pressure as blood serum and is therefore suitable as an isotonic solution for intravenous injection or infusion. Any other osmotically effective substances may also be used for isotonization as long as they are physiologically safe and well tolerated, such as glucose, glucose substitutes (fructose, sorbitol, xylitol) or glycerol. In another preferred embodiment, the pharmaceutical formulations may additionally contain further plasma-adapted electrolytes. The preparation of such isotonic formulations is known to the skilled person. An example of an isotonic solution with plasma-adapted electrolytes is the so-called Tyrode solution. It contains 0.8 g of NaCl, 0.02 g of KCl, 0.02 g of $CaCl_2$, 0.01 g of $MgCl_2$, 0.005 g of $NaH_2PO_4$, 0.1 g of $NaHCO_3$ and 0.1 g of glucose in 100 ml of distilled water. Another example is the so-called Ringer solution which contains 0.8% sodium chloride, 0.02% potassium chloride, 0.02% calcium chloride and 0.1% sodium hydrogencarbonate. Of course, the anions of the electrolytes may also be replaced by metabolizable anions; thus, for example, the sodium hydrogencarbonate in the Ringer solution may be replaced by 0.3 or 0.6% sodium lactate. A corresponding electrolyte composition or solution is known to the skilled person as "Ringer lactate". Further metabolizable anions which may be used alone or in combination are acetate (e.g., "Ringer acetate") or malate.

In another embodiment of the invention, the pharmaceutical formulations may also be in the form of hypertonic solutions. Hypertonic solutions are those having a higher osmotic pressure than that of the human blood. The application of hypertonic pharmaceutical formulations may be advantageous in certain clinical pictures. The required high osmotic pressures of hypertonic solutions is adjusted by adding corresponding amounts of osmotically effective substances, e.g., by sodium chloride, which may be used in concentrations of up to 7.5% and more for this purpose.

To avoid and reduce the risk of infections, the pharmaceutical formulations according to the invention are preferably subjected to sterile filtration or heat sterilization. Particularly suitable for the sterile filtration of aqueous or colloidal aqueous pharmaceutical formulations according to the invention are fine-pore filter cartridges, such as those provided by the company Sartorius under the trade name SARTPORE. Such filter cartridges with a pore diameter of 0.2 μm are suitable, for example. In addition, the pharmaceutical formulations according to the invention may be subjected to heat sterilization without the hydroxyethylstarches being adversely affected. Preferably, the heat sterilization is performed at a temperature above 100° C., more preferably from 105 to 150° C., especially from 110 to 130° C., for example, 121° C., for a period of up to 30 minutes, preferably up to 25 minutes, especially from 18 to 22 minutes.

In a preferred embodiment, the pharmaceutical formulation is a volume replacement. Volume replacements are used for replacing intravascular fluid in animal and human organisms. Volume replacements are used, in particular, in the prophylaxis and therapy of hypovolemia. It is not critical whether the hypovolemia results from the immediate loss of blood or body fluids, such as in acute bleeding, traumas, surgery, burns etc., or from disturbed distributions between macro- and microcirculation, such as in sepsis, or from vasodilation, such as during the initiation of anesthesia. The volume replacements are further classified into the so-called plasma replacements and the so-called plasma expanders. For the plasma replacements, the intravascularly applied volume of the agent also corresponds to the volume supplied to the vessels. In contrast, for the plasma expanders, the intravascularly applied liquid volume of the expander is lower than the volume actually supplied to the vessels. This phenomenon is based on the fact that the use of plasma expanders disturbs the oncotic equilibrium between the intra- and extravascular spaces and additional liquid volume flows from the extravascular space into the vascular system to be treated.

Plasma expanders are distinguished from plasma replacements essentially by the fact that the concentration of the hydroxyethylstarches according to the invention contained therein is increased and/or the concentration of the respective electrolytes causes an oncotic and/or osmotic imbalance.

The pharmaceutical formulation according to the invention may further contain a pharmaceutically active ingredient or combinations of active ingredients and thus serve as a medium for administering the active ingredients dissolved therein, especially by injection and infusion.

The present invention further relates to the use of a pharmaceutical formulation according to the invention for the preparation of a volume replacement or plasma replacement or plasma expander.

More preferably, the pharmaceutical formulations according to the invention may be used as a volume replacement or plasma replacement or plasma expander. Preferably, the pharmaceutical formulations serve for maintaining normovolemia. The maintaining of normovolemia is of particular importance for hemodynamic stability, which has a critical influence on the human or animal organism, for example, with respect to the blood pressure, the diuresis rate or the heart rate. In order to compensate a loss of intravascular liquid as quickly as possible and restore normovolemia, the pharmaceutical formulations according to the invention have proven particularly advantageous, because as compared to the plasma replacements known in the prior art, especially low-molecular weight HES solutions, such as HES 130/0.4, they have an extended plasma half life, especially in the critical phase immediately after infusion. The pharmaceutical formulations according to the invention are also advantageous, in particular, because it has surprisingly been found that the blood and/or plasma viscosity is not increased when the compositions are used, in contrast to the statement made in U.S. Pat. No. 5,502,043 for high-molecular weight HES, and because blood coagulation is inhibited less as compared to other high-molecular weight formulations. The fact that the plasma viscosity surprisingly is not increased also provides for an improvement of microcirculation and for an improved nutritive oxygen supply to the vessels.

The invention further relates to the use of the pharmaceutical formulation according to the invention for maintaining normovolemia and/or for improving the macro- and microcirculation and/or for improving the nutritive oxygen supply and/or for stabilizing hemodynamics and/or for improving the volume efficiency and/or for reducing the plasma viscosity and/or for increasing anemia tolerance and/or for hemodilution, especially for therapeutic hemodilution in disturbed blood supply and arterial, especially peripheral arterial, occlusive diseases.

The pharmaceutical formulations according to the invention or the hydroxyethylstarch according to the invention are preferably used for the preparation of medicaments, especially medicaments for maintaining normovolemia and/or for improving the macro- and microcirculation and/or for improving the nutritive oxygen supply and/or for stabilizing hemodynamics and/or for improving the volume efficiency and/or for reducing the plasma viscosity and/or for increasing anemia tolerance and/or for hemodilution, especially for therapeutic hemodilution in disturbed blood supply and arterial, especially peripheral arterial, occlusive diseases.

In addition, the pharmaceutical formulations according to the invention or the hydroxyethylstarches according to the invention are advantageously employed in methods for treating the maintenance of normovolemia and/or for improving the macro- and microcirculation and/or for improving the nutritive oxygen supply and/or for stabilizing hemodynamics and/or for improving the volume efficiency and/or for reducing the plasma viscosity and/or for increasing anemia tolerance and/or for hemodilution, especially for therapeutic hemodilution in disturbed blood supply and arterial, especially peripheral arterial, occlusive diseases.

The present invention further relates to a kit comprising separately:
  (i) a hydroxyethylstarch according to the invention;
  (ii) a sterile salt solution, preferably sodium chloride solution; and optionally
  (iii) a pharmaceutically active ingredient or a combination of active ingredients.

In a preferred embodiment, the kit according to the invention includes the individual components (i), (ii) and optionally (iii) in separated compartments in a multi-compartment bag, wherein all components may be separated, or certain components, such as (i) and (ii), may be contained together in one compartment.

The invention is further illustrated by the following Examples.

PREPARATION EXAMPLES FOR HES RAW MATERIALS

Example 1

Preparation of HES Raw Materials with Identical MS and $C_2/C_6$ Ratios but Different Molecular Weights The HES species described in the experimental part for the in vivo studies were prepared from one reaction charge by fractional hydrolysis. For this purpose, the following procedure was adopted. With vigorous stirring, 30 kg of thin boiling waxy maize starch was suspended in 52.2 kg of wfi (water for injection) at room temperature. In order to hydrate the starch optimally, the suspension was subsequently gelatinated by heating it to at least 85° C. After repeatedly inertizing the suspension by sparging with nitrogen for 10 min followed by evacuation, the starch was activated by adding 5.1 kg of NaOH. Subsequently, 4.159 kg of cooled ethylene oxide in liquid form was introduced into the reactor, and the temperature was slowly increased to 40° C., and the reaction mixture was left at that temperature for 2 hours with constant stirring. Unreacted ethylene oxide was removed from the reaction charge by repeatedly inertizing as described above. Then, three HES preparations with identical MS and $C_2/C_6$ ratios but different Mw were prepared from this raw HES by stepwise acidic hydrolysis. For reducing the molecular weight, the solution was adjusted to pH 2.0 with 20% HCl, heated up to 75±1° C. and left at that temperature until the average molecular weight Mw of the HES colloid as determined by means of GPC-MALLS had decreased to 865 kD. One third of the hydrolysis charge was removed from the reactor and immediately cooled down to a temperature of below 50° C. After the solution was decolorized by treatment with active charcoal, the solution was filtered by means of commercially available prefilters and sterile filters and, after being diluted to 12% by ultrafiltration (UF), purified. Thus, polyethersulfone membranes of the company Millipore with a cut-off of 10 kD were used. In the course of the UF, the Mw is slightly increased due to the partial elimination of the low-molecular weight HES fraction. This increase depends on the starting Mw of the colloid preparation but mainly on the declared cut-off of the UF membrane employed and the UF membrane lot employed. In order to achieve a desired target molecular weight after the UF, the Mw shift during the UF must be preliminarily established experimentally with the UF membrane lot employed. It is also to be noted that the hydrolysis continues from the time of sampling for determining the Mw during the acidic hydrolysis until the established Mw value has been obtained. Therefore, the decrease of the Mw is to be monitored systematically throughout the hydrolysis period, and the time at which the target Mw will be reached is to be estimated by extrapolation of the Mw over time. Then, the hydrolysis is stopped at this extrapolated time. The hydrolysis charge remaining after the first third has been removed was continued in the meantime until the average molecular weight Mw had decreased to 460 kD. Subsequently, the second third was processed in the same way as the first third. In parallel, the remaining third was further hydrolyzed to a Mw of 95 kD and subjected to the same processing procedure as the other two partial charges. From partial charge 1, HES 900/0.42 ($C_2/C_6$ ratio=4.83) could be obtained, from partial charge 2, HES 500/0.42 ($C_2/C_6$ ratio=4.83) could be obtained, and from partial charge 3, HES 130/0.42 ($C_2/C_6$ ratio=4.83) could be obtained.

After the ultrafiltration was completed, the colloid concentration was adjusted to 6%, and the pH value to 5.5, the solution was isotonized by adding NaCl, filled in glass bottles at 500 ml each, and sterilized at 121° C. for 20 minutes.

Example 2

Preparation of Further HES Raw Materials

In order to produce HES colloids with other molar substitutions and $C_2/C_6$ ratios, a number of further experiments were performed on the same scale, the amount of ethylene oxide being varied accordingly. In addition, the acidic hydrolysis was stopped when different Mw (target Mw) were reached. These experiments are summarized in the following Table 1:

TABLE 1

|  | Ex. 1 | Ex. 2 | Ex. 3 | Ex. 4 | Ex. 5 |
|---|---|---|---|---|---|
| Reaction conditions |  |  |  |  |  |
| Starch (kg) | 30.0 | 30.0 | 30.0 | 30.0 | 30.0 |
| WFI (kg) | 52.0 | 52.0 | 52.0 | 52.0 | 52.0 |
| NaOH 50% (kg) | 9.5 | 4.7 | 4.7 | 9.5 | 4.7 |
| Ethylene oxide (kg) | 4.0 | 3.6 | 4.4 | 4.5 | 3.8 |
| Target Mw (after acidic hydrolysis) (kDa) | 1500 | 990 | 885 | 770 | 665 |
| HES characteristics |  |  |  |  |  |
| MS (mol/mol) | 0.39 | 0.40 | 0.45 | 0.46 | 0.42 |
| Mw after UF (kDa) | 1520 | 1050 | 915 | 795 | 710 |
| $C_2$:$C_6$ ratio | 2.3 | 6.0 | 5.9 | 2.2 | 6.1 |

Example 3

Influence of the Molar Ratio of NaOH to Starch during the Hydroxyethylation on the $C_2/C_6$ Ratio In order to demonstrate the controllability of the $C_2/C_6$ ratio by the molar ratio of NaOH to anhydroglucose units of the starch, 30 kg of thin boiling waxy maize starch was admixed with different amounts of NaOH and reacted with ethylene oxide at 40° C. In Table 2, the amounts of reagents employed and the $C_2/C_6$ ratios as well as the MS of the HES products obtained by this reaction are listed. As can be seen, the $C_2/C_6$ ratio decreases as the ratio of NaOH to starch increases. This is due to the fact that the base-catalyzed hydroxyethylation of the starch at a low NaOH concentration is preferably effected at the hydroxyethyl groups in 2 position of the anhydroglucose units, which are the most reactive. By higher NaOH concentrations, the $C_6$ hydroxy groups, which are per se less reactive, are also activated sufficiently to become efficiently hydroxyethylated.

TABLE 2

Control of the $C_2/C_6$ ratio during hydroxyethylation

| Trial | WFI [kg] | Starch [kg] | NaOH (50% by weight) [kg] | Molar ratio of NaOH to starch | Ethylene oxide [kg] | MS | $C_2/C_6$ |
|---|---|---|---|---|---|---|---|
| #1 | 50 | 30 | 1.5 | 0.1 | 4.0 | 0.4 | 12 |
| #2 | 50 | 30 | 4.5 | 0.3 | 3.8 | 0.4 | 7 |
| #3 | 50 | 30 | 11.1 | 0.75 | 4.4 | 0.4 | 3 |

Preparations Examples of HES Finished Products

In the following Table 3, the formulations for the preparation of various HES solutions are stated. The HES was employed as an HES concentrate after ultrafiltration. The amount of HES concentrate required for the preparation of a 6% or 10% HES solution was determined by rule-of-three calculation. Another possibility is to use spray-dried HES, which does not pose any problem to the skilled person who has a spraying tower at his disposal. The HES employed had a molecular weight of 900 kD and an MS of 0.42.

In a 200 l reaction tank, the respectively required amount of HES concentrate and the amounts of salts and NaOH solution as stated in the Table were weighed, and the salts were dissolved with stirring. After adjusting the pH of solutions 1, 4, 5, 7 and 8 to 5.5 and of solutions 2, 3, 6 to 6.0, water for injection (WFI) was added in such an amount that the theoretical Na concentrations according to the specification were reached.

As obvious to the skilled person, the formulations can be varied widely by changing the proportions of the stated active ingredients or auxiliary agents and by omitting or adding further substances, and if other HES species are used, corresponding solutions can be prepared with those as well.

TABLE 3

|  | 1 | 2 | 3 | 4 | 5 | 6 | 7 | 8 |
|---|---|---|---|---|---|---|---|---|
| Preparation formulations |  |  |  |  |  |  |  |  |
| HES [g/l] | 60 | 60 | 60 | 60 | 100 | 100 | 100 | 100 |
| NaCl [g/l] | 9.00 | 6.369 | 17.37 | 100.0 | 9.00 | 6.369 | 30.00 | 60.00 |
| KCl [g/l] | 0 | 0.373 | 0.373 | 0 | 0 | 0.373 | 0 | 0 |
| $MgCl_2$ [g/l] | 0 | 0.203 | 0.203 | 0 | 0 | 0.203 | 0 | 0 |
| $CaCl_2$ [g/l] | 0 | 0.294 | 0.294 | 0 | 0 | 0.294 | 0 | 0 |
| Na acetate [g/l] | 0 | 5.032 | 5.032 | 0 | 0 | 5.032 | 0 | 0 |
| Results of analyses of the solutions |  |  |  |  |  |  |  |  |
| HES [%] | 6.0 | 6.1 | 6.0 | 5.9 | 10.0 | 10.1 | 9.9 | 10.0 |
| Na [mM] | 153.9 | 146.1 | 334.3 | 1711 | 153.7 | 146.0 | 512.5 | 1026 |
| K [mM] | 0 | 5.1 | 5.0 | 0 | 0 | 5.0 | 0 | 0 |
| Mg [mM] | 0 | 1.0 | 0.9 | 0 | 0 | 1.0 | 0 | 0 |
| Ca [mM] | 0 | 2.1 | 2.0 | 0 | 0 | 2.0 | 0 | 0 |
| Cl [mM] | 154.8 | 120.2 | 308.5 | 1712 | 154.8 | 120.1 | 513.7 | 1028 |
| Acetate [mM] | 0 | 37.0 | 37.0 | 0 | 0 | 37.0 | 0 | 0 |
| pH | 5.5 | 6.0 | 5.9 | 5.3 | 5.4 | 6.1 | 5.4 | 5.5 |

Measuring Methods of the Application Examples

In the following, the measuring methods are described with which the blood and plasma samples were examined.

Native Blood Measurements:

Blood samples with added citrate were treated in the laboratory as follows:

One sample was used immediately for the measurement of blood viscosity (Rheostress® 1, Thermo-Haake, Karlsruhe, Germany) with linearly increasing shear rates of 1 to 240 per second. The viscosity was examined at shear rates of 1 per second and 128 per second. Before analysis on a Thromboelastograph® (TEG®, Haemoscope Corporation, Niles, Ill.), the blood samples were incubated in a water bath of 37° C. for one hour. The blood recalcification and the TEG® measurements were performed in accordance with the manufacturer's instructions. The coagulation index (CI), which summarizes several partial functions of thromboelastography, was determined.

Plasma Measurements:

The blood samples were centrifuged at 4° C. and 3000 rpm (Rotana/RP, Hettich, Bäch, Switzerland) for 15 minutes. The plasma viscosity was measured as described above for the blood determination.

The prothrombin time (PT) and the activated partial thromboplastin time (aPTT) were determined by means of an automated coagulation analyzer (BCS, Dade Behring, Marburg, Germany) using a PT reagent containing a recombinant tissue factor (Innovin®, Dade Behring) and an aPTT reagent containing ellagic acid (Actin FS®, Dade Behring). PT values were converted to INR values based on the ISI values supplied by the manufacturer. The functional activity of von Willebrand factor (vWF) was determined by means of a commercial ristocetin cofactor assay (vWF RCA, Dade Behring) in an automated coagulation analyzer (BCS, Dade Behring). The vWF activity was established by the ability to agglutinate human thrombocytes in the presence of ristocetin. Agglutination was determined by means of turbidity measurements with a coagulation analyzer. Antigen vWF was detected by a commercial ELISA kit (Asserachrom vWF antigenic, Roche Diagnostics, Rotkreuz, Switzerland) in accordance with the manufacturer's instructions.

The HES concentration was quantified after extraction from blood plasma and hydrolysis into glucose monomer units (H. Forster et al., Infusionstherapie 1981; 2: 88-94). The plasma samples (1 ml) were incubated at 100° C. for 60 minutes after being admixed with 0.5 ml of KOH solutions 35% (w/w) (Fluka, Buchs, Switzerland). The HES was precipitated by adding 10 ml of ice-cold absolute ethanol (Fluka, Buchs, Switzerland) to the supernatant of the reaction mixture, followed by acid hydrolysis in 2 N HCl (Fluka, Buchs, Switzerland) for 60 minutes at 100° C. The glucose determination was effected by using an enzyme test kit based on hexokinase/glucose 6-phosphatase (Boehringer Mannheim, Darmstadt, Germany).

The calculation of the pharmacokinetic parameters was effected with the assumption of a two-compartment model with a constant infusion rate using the actual dosages and infusions periods (WinNonlin, Version 4.1, Pharsight Corp., Mountainview, Calif.).

Statistical Analysis:

The values were stated as mean value ± standard deviation. The two HES solutions having a high molecular weight (500 and 900 kD) were compared with the low-molecular weight (130 kD) solution by means of the JMP 5.1 statistics package (SAS Institute, Inc., Cary, N.C.). The interaction of solution and time effects was tested by means of two-sided ANOVA analysis taking into account the Bonferroni correction. For the statistical analysis of the pharmacokinetic parameters, Student's unpaired t test was used. A p of <0.05 was considered statistically significant.

Application Examples

For the in vivo experiments described below, hydroxyethylstarches according to the invention having average molecular weights (Mw) of 500,000 and 900,000 Daltons and identical molar substitutions (MS=0.42) and identical $C_2/C_6$ ratios (4.83) (in the following Application Examples referred to as HES 500/0.42 and HES 900/0.42, respectively) were used (see Preparation Example for HES raw materials). Both hydroxyethylstarches (HES 900/0.42 and HES 500/0.42) were dissolved in 0.9% saline at a concentration of 6% using 0.2 μm filter cartridges (Sartpore; Sartorius), subjected to sterile filtration, filled in glass bottles and heat-sterilized at 121° C. for 15 minutes. A low-molecular weight hydroxyethylstarch (Mw=130,000 Daltons) with identical MS and $C_2/C_6$ ratio (in the following Application Examples referred to as HES 130/0.42), which was also in 6% concentration in 0.9% saline, served as a comparative solution. As described, it was obtained from the same reaction charge as the high-molecular weight starches according to the invention, from which it was therefore distinguished only by the molecular weight.

Examination of Plasma Elimination and its Influence on Blood Coagulation 30 pigs were randomized in 3 groups of 10 animals each. One group received an intravenous infusion of HES 900/0.42, another received an infusion of HES 500/0.42, and the third received an infusion of HES 130/0.42 for comparison. In all cases, the dose was 20 ml/kg body weight of the HES solutions, which were 6% each, and the infusion took 30 minutes. For the infusion and the subsequent blood sampling, the animals were anesthetized (halothane anesthesia) and subjected to controlled respiration. Blood samplings were effected before the beginning of infusion, after 5, 20, 40, 60, 120 and 240 minutes as well as 24 hours after the end of the infusion. In the blood samples and plasma samples obtained therefrom, the following parameters were determined: blood and plasma viscosities, HES concentration, prothrombin time, partial thromboplastin time, von Willebrand factor, factor VIII and ristocetin cofactor as well as the usual thromboelastographic characteristics. From the course of the HES concentrations from the end of the infusion until 24 h thereafter, the area under the concentration vs. time curve (=AUC, area under the curve), the α and β half lives and the clearance were calculated. The calculation of AUC was effected according to the log-linear trapezoidal rule, and the calculation of the remaining pharmacokinetic parameters was based on a two compartment model. This yields 2 half lives, α and β, the α half life designating the transition of the HES from the central compartment (corresponds essentially to the intravascular space) into the peripheral compartment, and the β half life designating the back distribution in the reverse direction.

The course of the HES concentration and the pharmacokinetic parameters showed a longer plasma residence time of the high-molecular weight variants (HES 900/0.42 and HES 500/0.42) as compared to the low-molecular weight HES (HES 130/0.42). Thus, the AUCs and α half lives were significantly larger or longer, respectively, in the high-molecular weight variants as compared to the lower-molecular weight control; accordingly, the clearance of the high-molecular weight HES types was significantly lower than that of the lower-molecular weight HES.

However, surprisingly and completely unlike previously known types of medium- or high-molecular weight HES (HES 200/0.5; HES 200/0.6; HES 450/0.7), there was no relevant differences in the plasma concentration at the time "24 hours after infusion" between the high-molecular weight variants according to the invention and the low-molecular weight comparative solution (cf. FIG. 1). This means that the high-molecular weight hydroxyethylstarches according to the invention have a significantly longer plasma residence time as compared to the lower-molecular weight comparative HES in the phase immediately after the infusion, which is critical to volume efficiency but that they have no tendency to accumulation in the circulation, in contrast to previously known high-molecular weight HES types. Instead, the HES variants according to the invention, like the lower-molecular comparative HES, had virtually completely disappeared from the circulation 24 hours after the infusion.

TABLE 4

| Solution | HES 130/0.42 | HES 500/0.42 | HES 900/0.42 |
|---|---|---|---|
| AUC (g · min/l) | 1156 ± 223 | 1542 ± 142** | 1701 ± 321** |
| CL (ml/min) | 39.1 ± 7.9 | 30.1 ± 5.4* | 26.0 ± 4.1** |
| $t_{1/2\alpha}$ (min) | 39.9 ± 10.7 | 53.8 ± 8.6* | 57.1 ± 12.3* |
| $t_{1/2\beta}$ (min) | 331.8 ± 100.0 | 380.6 ± 63.3 | 379.9 ± 75.8 |

Table 4: Area under the concentration vs. time curve (AUC), clearance (CL), α and β half lives ($t_{1/2\alpha}$ and $t_{1/2\beta}$) after infusion of 20 ml/kg each of 6% HES 130/0.42, 6% HES 500/0.42 and 6% HES 900/0.42 in pigs.

to HES 130/0.42 (see also Table 4: pharmacokinetic parameters); however, in the end phase of elimination, i.e., 24 h after the end of the infusion, there was no longer a relevant difference between the plasma concentrations (the average concentrations were below 0.2 g/l, which is within the range of the determination limit).

Thus, it has been found that the hydroxyethylstarches according to the invention on the one hand have a longer initial plasma half life as compared to currently known lower-molecular weight reference solutions (HES 130/0.42) but on the other hand can be eliminated from the circulation within 24 hours after infusion as readily as the latter lower-molecular weight comparative preparations, which are advantageous in this respect.

Also, the coagulation analyses performed (plasmatic coagulation tests, thromboelastography, determination of vWF concentrations) yielded unexpected results, because the results were completely different from those which could be achieved previously with high-molecular weight HES preparations. While already medium-molecular weight and, to a much more pronounced extent, high-molecular weight hydroxyethylstarches usually have previously shown a far stronger impairment of blood coagulation in terms of hypocoagulability as compared to lower-molecular weight HES solutions (J. Treib et al., Intensive Care Med. (1999), pp. 258 to 268; R. G. Strauss et al., Transfusion (1988), pp. 257-260), no significant differences were found between the high-molecular weight HES preparations according to the invention and the known lower-molecular weight comparative solution (cf. Table 5).

TABLE 5

| Parameter | Solution | before infusion | after infusion 5 min | after infusion 1 hour | after infusion 2 hours | after infusion 4 hours | after infusion 24 hours | p value |
|---|---|---|---|---|---|---|---|---|
| PT (s) | HES 130/0.42 | 8.57 ± 0.73 | 9.15 ± 0.66 | 9.00 ± 0.70 | 9.06 ± 0.67 | 8.77 ± 0.42 | 9.30 ± 0.64 | — |
|  | HES 500/0.42 | 9.32 ± 1.90 | 9.08 ± 0.49 | 8.97 ± 0.56 | 8.80 ± 0.33 | 8.57 ± 0.37 | 9.38 ± 0.58 | 0.533 |
|  | HES 900/0.42 | 8.59 ± 1.06 | 8.66 ± 0.51 | 8.56 ± 0.56 | 8.40 ± 0.27 | 8.21 ± 0.27 | 9.42 ± 0.51 | 0.068 |
| aPTT | HES 130/0.42 | 12.19 ± 1.83 | 14.19 ± 4.21 | 13.68 ± 3.57 | 13.59 ± 1.57 | 13.11 ± 1.10 | 14.58 ± 3.01 | — |
| (s) | HES 500/0.42 | 11.97 ± 1.00 | 13.37 ± 1.12 | 12.65 ± 0.73 | 13.04 ± 1.31 | 13.17 ± 1.31 | 13.72 ± 1.40 | 0.893 |
|  | HES 900/0.42 | 11.94 ± 1.31 | 12.59 ± 1.16 | 13.10 ± 1.62 | 12.87 ± 1.06 | 12.78 ± 2.02 | 13.37 ± 1.50 | 0.706 |
| CI | HES 130/0.42 | 4.53 ± 1.33 | 3.30 ± 0.91 | 4.18 ± 0.91 | 4.81 ± 0.63 | 4.48 ± 0.65 | 5.22 ± 0.35 | — |
|  | HES 500/0.42 | 5.04 ± 0.81 | 2.88 ± 1.28 | 4.47 ± 0.77 | 4.71 ± 0.65 | 4.18 ± 0.98 | 5.14 ± 0.79 | 0.303 |
|  | HES 900/0.42 | 5.35 ± 0.79 | 3.28 ± 1.18 | 4.47 ± 0.93 | 4.93 ± 0.82 | 4.68 ± 1.03 | 5.53 ± 0.55 | 0.468 |
| vWF | HES 130/0.42 | 33.41 ± 10.18 | 30.09 ± 7.68 | 32.20 ± 8.63 | 33.59 ± 10.94 | 40.91 ± 10.48 | 28.80 ± 6.84 | — |
| funct. | HES 500/0.42 | 32.11 ± 4.85 | 25.38 ± 3.84 | 27.65 ± 4.32 | 30.80 ± 4.67 | 37.94 ± 4.65 | 23.04 ± 4.19 | 0.853 |
| (%) | HES 900/0.42 | 30.48 ± 3.95 | 24.78 ± 3.35 | 27.14 ± 4.14 | 31.41 ± 4.83 | 37.87 ± 8.06 | 24.84 ± 6.74 | 0.768 |
| vWF | HES 130/0.42 | 46.10 ± 8.45 | 35.80 ± 4.83 | 39.40 ± 8.42 | 40.10 ± 9.21 | 44.30 ± 6.80 | 38.22 ± 5.54 | — |
| antig. | HES 500/0.42 | 42.80 ± 4.13 | 37.90 ± 7.37 | 35.50 ± 4.22 | 37.60 ± 7.41 | 39.80 ± 10.65 | 38.00 ± 8.15 | 0.499 |
| (%) | HES 900/0.42 | 48.10 ± 19.56 | 33.30 ± 5.48 | 35.70 ± 5.89 | 37.80 ± 4.26 | 42.00 ± 4.85 | 41.67 ± 6.08 | 0.473 |

The significance test was effected between HES 500 and HES 900 each in comparison with HES 130/0.42 by means of a Student's unpaired t test; *: p<0.01; **: p<0.001.

The high-molecular weight HES species (HES 500/0.42 and HES 900/0.42) showed significantly larger areas under the concentration vs. time curve (AUC), corresponding to a longer residence time in the intravascular space, significantly longer initial plasma half lives ($t_{1/2\alpha}$) and significantly lower clearance rates as compared to lower-molecular weight ones (HES 130/0.42).

FIG. 1 shows the course of the concentration of low-molecular weight HES (HES 130/0.42) and high-molecular weight HES (HES 500/0.42 and ES 900/0.42) in the plasma after infusion of 20 ml/kg of the respective HES solution in pigs. Initially, HES 500/0.42 and HES 900/0.42 were eliminated more slowly from the intravascular space as compared Table 5 shows the time course of the plasmatic coagulation parameters prothrombin time (PT), activated partial thromboplastin time (aPTT), functional activity of von Willebrand factor (vWF functional) and antigenic concentration of von Willebrand factor (vWF antigenic) and the time course of the coagulation index (CI) of thromboelastography after infusion of 20 ml/kg each of 6% HES 130/0.42, 6% HES 500/0.42 and 6% HES 900/0.42, respectively, in pigs. The test for statistic significance (interaction of solution and time effects) was performed between HES 500/0.42 and HES 900/0.42, respectively as compared to HES 130/0.42, by means of two-sided ANOVA. Despite higher molecular weights, higher concentrations and a longer residence time in plasma (cf. FIG. 1 and Table 4), the high-molecular weight HES species according to the invention (HES 500/0.42 and HES 900/0.42) did not influence blood coagulation to any higher extent as low-molecular weight HES (HES 130/0.42).

In other words, despite a longer plasma residence time achieved by increasing the molecular weight, the hydroxyethylstarches according to the invention did not show the drawbacks of known high-molecular weight solutions, such as the impairment of blood coagulation conferred by them.

In addition, it was surprisingly found in the animal experimental studies that the high-molecular weight hydroxyethylstarches according to the invention did not increase the blood and plasma viscosity as compared with lower-molecular weight HES, in contrast to known high-molecular weight hydroxyethylstarches. At low shear forces, a lower viscosity was even found among the hydroxyethylstarches according to the invention than among the lower-molecular weight HES (cf. Table 6: plasma viscosity).

$C_2/C_6$ ratio on blood coagulation was especially tested, i.e., also by means of thromboelastography. For this purpose, three high-molecular weight HES solutions (Mw: 800 kD) with a low MS (0.4) and a low (3:1), medium (7:1) or high (12:1) $C_2/C_6$ ratio were prepared and examined as follows. From 30 male and female surgical patients (exclusion criteria: known coagulation disorders, treatment with blood coagulation inhibitors, ingestion of acetylsalicylic acid or other non-steroidal anti-inflammatory medicaments within 5 days before the surgery), a blood sample was taken during the initiation of anesthesia. In every blood sample, the coagulation as measured by means of thromboelastography, i.e., in undiluted blood and after in vitro hemodilution (20%, 40% and 60%) with each of three HES solutions (HES 800/0.4/3:1; HES 800/0.4/7:1 and HES 800/0.4/12:1). As with the in vivo studies, the parameter determined was the coagulation index

TABLE 6

| Parameter | Solution | before infusion | after infusion 5 min | after infusion 20 min | after infusion 40 min |
|---|---|---|---|---|---|
| Plasma visc. | HES 130/0.42 | 0.016383 ± 0.008241 | 0.012721 ± 0.005245 | 0.012620 ± 0.004280 | 0.012875 ± 0.003349 |
| $\gamma = 1/s$ | HES 500/0.42 | 0.012313 ± 0.005196 | 0.012582 ± 0.001873 | 0.013591 ± 0.001912 | 0.012936 ± 0.002555 |
| (mPas) | HES 900/0.42 | 0.016869 ± 0.007240 | 0.012375 ± 0.002487 | 0.015985 ± 0.005659 | 0.015968 ± 0.006499 |
| Plasma visc. | HES 130/0.42 | 0.001208 ± 0.000097 | 0.001327 ± 0.000644 | 0.001138 ± 0.000089 | 0.001167 ± 0.000105 |
| $\gamma = 128/s$ | HES 500/0.42 | 0.001246 ± 0.000212 | 0.001110 ± 0.000045 | 0.001125 ± 0.000058 | 0.001106 ± 0.000037 |
| (mPas) | HES 900/0.42 | 0.001271 ± 0.000078 | 0.001141 ± 0.000064 | 0.001174 ± 0.000065 | 0.001166 ± 0.000075 |

| Parameter | Solution | after infusion 1 hour | after infusion 2 hours | after infusion 4 hours | after infusion 24 hours | p value |
|---|---|---|---|---|---|---|
| Plasma visc. | HES 130/0.42 | 0.014928 ± 0.003944 | 0.018318 ± 0.006364 | 0.015097 ± 0.007475 | 0.024577 ± 0.008847 | — |
| $\gamma = 1/s$ | HES 500/0.42 | 0.013070 ± 0.002860 | 0.011384 ± 0.005949 | 0.013736 ± 0.003974 | 0.015434 ± 0.004320 | 0.005 |
| (mPas) | HES 900/0.42 | 0.013678 ± 0.002252 | 0.014217 ± 0.003234 | 0.013557 ± 0.003713 | 0.015556 ± 0.004308 | 0.003 |
| Plasma visc. | HES 130/0.42 | 0.001142 ± 0.000084 | 0.001272 ± 0.000217 | 0.001232 ± 0.000136 | 0.001229 ± 0.000102 | — |
| $\gamma = 128/s$ | HES 500/0.42 | 0.001112 ± 0.000048 | 0.001206 ± 0.000114 | 0.001183 ± 0.000112 | 0.001257 ± 0.000068 | 0.386 |
| (mPas) | HES 900/0.42 | 0.001146 ± 0.000055 | 0.001304 ± 0.000224 | 0.001228 ± 0.000096 | 0.001247 ± 0.000104 | 0.444 |

Table 6 shows the time course of plasma viscosity at low and high shear forces ($\gamma=1/s$ and $\gamma=128/s$ after infusion of 20 ml/kg each of 6% HES 130/0.42, 6% HES 500/0.42 and 6% HES 900/0.42, respectively, in pigs. The test for statistic significance (interaction of solution and time effects) was performed between HES 500/0.42 and HES 900/0.42, respectively as compared to HES 130/0.42, by means of two-sided ANOVA and did not show any differences between the high-molecular weight HES species (HES 900 and HES 500) and the lower-molecular weight HES (HES 130). At lower shear forces, the interaction between the solution and time effects in the plasma viscosity proved to be lower among the high-molecular weight HES species (HES 500/0.42 and HES 900/0.42) as compared to the lower-molecular weight HES (HES 130/0.42). However, this was due to the time rather than the solution effect. At high shear forces, there was no difference; in particular, the plasma viscosity was not higher among the high-molecular weight HES species (HES 900/0.42 and HES 500/0.42) than among lower-molecular weight HES (HES 130/0.42).

Thus, the plasma viscosity does not increase among the HES solutions according to the invention. The fact that no increase of plasma viscosity was observed is surprising because hydroxyethylstarch with a comparable molecular weight of 500,000 as disclosed in U.S. Pat. No. 5,502,043 (Comparative Example 3) exhibited an increase of plasma viscosity. If the viscosity is not increased, this leads to undisturbed capillary perfusion (microcirculation) and an improved nutritive oxygen supply to the tissues.

In addition to the above described in vivo studies, in vitro studies were also performed in which the influence of the (CI), which summarizes the individual partial functions of thromboelastography. The mean values (±SD) of the CI values found are represented in the following Table 7, i.e., as deviation from the CI in the respective undiluted blood sample.

TABLE 7

|  | HES 800/0.4/3:1 | HES 800/0.4/7:1 | HES 800/0.4/12:1 |
|---|---|---|---|
| 20% hemodilution | −2.32 | −2.86 | −3.35 |
|  | (1.20) | (1.22) | (1.07) |
| 40% hemodilution | −5.91 | −6.17 | −6.50 |
|  | (1.68) | (2.03) | (1.69) |
| 60% hemodilution | −9.71 | −10.37 | −10.55 |
|  | (2.70) | (3.05) | (2.60) |

In all hemodilution stages, the CI relative to the CI of the native blood was decreased the less, i.e., the blood coagulation influenced the less, the lower the $C_2/C_6$ ratio of the HES used for hemodilution was. The solution effect between the hemodilution series was significantly different (p<0.05; ANOVA). The results show that a decrease of the $C_2/C_6$ ratio of hydroxyethylstarches is favorable for their influence on blood coagulation, namely in such terms that blood coagulation is inhibited less at a lower $C_2/C_6$ ratio as compared to a high one. This is important because HES solutions are employed, inter alia, as plasma replacements after traumatically or surgically caused bleedings, and in this situation, they must not add to the blood loss by inhibiting blood coagulation. The results of the above described study further show that the $C_2/C_6$ ratio of HES solutions has an intrinsic effect on blood coagulation which is independent of other molecular parameters of HES and their behavior in the circulation. This has not been known to date.

The invention claimed is:

1. A pharmaceutical formulation for use in at least one of maintaining normovolemia, improving macro and microcirculation, improving nutritive oxygen supply, stabilizing hemodynamics, improving volume efficiency, reducing plasma viscosity, increasing anemia tolerance, and performing hemodilution, the pharmaceutical formulation comprising a hydroxyethylstarch comprising an average molecular weight, Mw, of greater than or equal to 500,000, a molar substitution MS of from 0.25 to 0.5 and a $C_2/C_6$ ratio of from 2 to below 8, wherein the hydroxyethylstarch in the formulation is in a concentration of up to 20%.

2. A pharmaceutical formulation for use in at least one of maintaining normonovolemia, improving macro and microcirculation improving nutritive oxygen supply, stabilizing hemodynamics, improving volume efficiency, reducing plasma viscosity, increasing anemia tolerance, and performing hemodilution, the pharmaceutical formulation comprising a hydroxyethylstarch comprising an average molecular weight. Mw, of greater than or equal to 500,000, a molar substitution MS of from 0.25 to 0.5 and a $C_2/C_6$ ratio of from 2 to below 8, wherein the hydroxyethylstarch is at least one of sterile filtered and heat sterilized.

3. A pharmaceutical formulation for use in at least one of maintaining normovolemia, improving macro and microcirculation, improving nutritive oxygen supply, stabilizing hemodynamics, improving volume efficiency reducing plasma viscosity, increasing anemia tolerance, and performing hemodilution, the pharmaceutical formulation comprising a hydroxyethylstarch comprising an average molecular weight, Mw, of greater than or equal to 500,000, a molar substitution MS of from 0.25 to 0.5 and a $C_2/C_6$ ratio of from 2 to below 8, and the pharmaceutical formulation further comprises at least one of the following active ingredients: sodium chloride, magnesium chloride, potassium chloride, calcium chloride and sodium acetate.

4. A method of preparing a plasma replacement or plasma expander, said method comprising the step of preparing a pharmaceutical formulation comprising a hydroxyethylstarch comprising an average molecular weight. Mw, of greater than or equal to 500,000, characterized by having a molar substitution MS of from 0.25 to 0.5 and a $C_2/C_6$ ratio of from 2 to below 8, and further comprising the step of filtrating and sterilizing the hydroxyethylstarch.

5. A method of preparing a plasma replacement or plasma expander, said method comprising the step of preparing a pharmaceutical formulation comprising a hydroxyethylstarch comprising an average molecular weight, Mw of greater than or equal to 500,000, characterized by having a molar substitution MS of from 0.25 to 0.5 and a $C_2/C_6$ ratio of from 2 to below 8, and wherein the pharmaceutical formulation further comprises at least one of the following active ingredients: sodium chloride, magnesium chloride, potassium chloride, calcium chloride and sodium acetate.

6. A kit comprising separately:
(i) a hydroxyethylstarch; and
(ii) a sterile salt solution
wherein the hydroxyethylstarch comprises an average molecular weight. Mw, of greater than or equal to 500,000, characterized by having a molar substitution MS of from 0.25 to 0.5 and a $C_2/C_6$ ratio of from 2 to below 8.

7. The kit of claim 6, wherein the sterile salt solution is sodium chloride solution.

8. The kit of claim 6 further comprising at least one of the following active ingredients: sodium chloride, magnesium chloride, potassium chloride, calcium chloride and sodium acetate.

9. The kit of claim 6, wherein the molar substitution MS is from 0.35 to 0.5.

10. The kit of claim 6, wherein the average molecular weight is from above 600,000 to 1,500,000.

11. The kit of claim 6, wherein the C2/C6 ratio is from 2 to 7.

12. The kit of claim 6, wherein the hydroxyethylstarch and the sterile salt solution are in separated compartments in a multi-compartment bag.

13. The kit of claim 8, wherein the hydroxyethylstarch, the sterile salt solution, and the at least one pharmaceutically active ingredient are in separated compartments in a multi-compartment bag.

14. The pharmaceutical formulation according to claim 1, wherein the pharmaceutical formulation is in the form of at least one of an aqueous solution and a colloidal aqueous solution.

15. The pharmaceutical formulation according to claim 1, wherein the pharmaceutical formulation further comprises sodium chloride.

16. The pharmaceutical formulation according to claim 1, wherein the pharmaceutical formulation further comprises plasma-adapted electrolytes.

17. The pharmaceutical formulation according to claim 1, wherein the pharmaceutical formulation is in the form of at least one of a buffered solution and a solution with metabolizable anions.

18. The pharmaceutical formulation according to claim 1, wherein the pharmaceutical formulation is in the form of a hypertonic solution.

19. The pharmaceutical formulation according to claim 1, wherein the hydroxyethylstarch is at least one of sterile filtered and heat sterilized.

20. The pharmaceutical formulation according to claim 1, characterized by being a volume replacement.

21. The pharmaceutical formulation according to claim 1, further comprising at least one of the following active ingredients: sodium chloride, magnesium chloride, potassium chloride, calcium chloride and sodium acetate.

22. The pharmaceutical formulation according to claim 2, wherein the pharmaceutical formulation is in the form of at least one of an aqueous solution and a colloidal aqueous solution.

23. The pharmaceutical formulation according to claim 2, wherein the hydroxyethylstarch in the formulation is in a concentration of up to 20%.

24. The pharmaceutical formulation according to claim 2, wherein the pharmaceutical formulation further comprises sodium chloride.

25. The pharmaceutical formulation according to claim 2, wherein the pharmaceutical formulation further comprises plasma-adapted electrolytes.

26. The pharmaceutical formulation according to claim 2, wherein the pharmaceutical formulation is in the form of at least one of a buffered solution and a solution with metabolizable anions.

27. The pharmaceutical formulation according to claim 2, wherein the pharmaceutical formulation is in the form of a hypertonic solution.

28. The pharmaceutical formulation according to claim 2, characterized by being a volume replacement.

29. The pharmaceutical formulation according to claim 2, further comprising at least one of the following active ingredients: sodium chloride, magnesium chloride, potassium chloride, calcium chloride and sodium acetate.

30. The pharmaceutical formulation according to claim 3, wherein the pharmaceutical formulation is in the form of at least one of an aqueous solution and a colloidal aqueous solution.

31. The pharmaceutical formulation according to claim 3, wherein the hydroxyethylstarch in the formulation is in a concentration of up to 20%.

32. The pharmaceutical formulation according to claim 3, wherein the pharmaceutical formulation further comprises plasma-adapted electrolytes.

33. The pharmaceutical formulation according to claim 3, wherein the pharmaceutical formulation is in the form of at least one of a buffered solution and a solution with metabolizable anions.

34. The pharmaceutical formulation according to claim 3, wherein the pharmaceutical formulation is in the form of a hypertonic solution.

35. The pharmaceutical formulation according to claim 3, wherein the hydroxyethylstarch is at least one of sterile filtered and heat sterilized.

36. The pharmaceutical formulation according to claim 3, characterized by being a volume replacement.

37. The method of claim 4, wherein the pharmaceutical formulation is in the form of at least one of an aqueous solution and a colloidal aqueous solution.

38. The method of claim 4, wherein the hydroxyethylstarch is in a concentration of up to 20%.

39. The method of claim 4, wherein the pharmaceutical formulation further comprises sodium chloride in the pharmaceutical formulation.

40. The method of claim 4, wherein the pharmaceutical formulation further comprises plasma-adapted electrolytes.

41. The method of claim 4, wherein the pharmaceutical formulation is in the form of at least one of a buffered solution and a solution with metabolizable anions.

42. The method of claim 4, wherein the pharmaceutical formulation is in a form of a hypertonic solution.

43. The method of claim 4, further comprising using the pharmaceutical formulation as a volume replacement.

44. The method of claim 4, wherein the pharmaceutical formulation further comprises at least one of the following active ingredients: sodium chloride, magnesium chloride, potassium chloride, calcium chloride and sodium acetate.

45. The method of claim 5, wherein the pharmaceutical formulation is in the form of at least one of an aqueous solution and a colloidal aqueous solution.

46. The method of claim 5, wherein the hydroxyethylstarch is in a concentration of up to 20%.

47. The method of claim 5, wherein the pharmaceutical formulation further comprises sodium chloride in the pharmaceutical formulation.

48. The method of claim 5, wherein the pharmaceutical formulation further comprises plasma-adapted electrolytes.

49. The method of claim 5, wherein the pharmaceutical formulation is in the form of at least one of a buffered solution and a solution with metabolizable anions.

50. The method of claim 5, wherein the pharmaceutical formulation is in a form of a hypertonic solution.

51. The method of claim 5, further comprising the step of filtrating and sterilizing thehydroxyethylstarch.

52. The method of claim 5, further comprising using the pharmaceutical formulation as a volume replacement.

* * * * *

UNITED STATES PATENT AND TRADEMARK OFFICE
CERTIFICATE OF CORRECTION

| | | |
|---|---|---|
| PATENT NO. | : 7,863,260 B2 | Page 1 of 1 |
| APPLICATION NO. | : 10/590462 | |
| DATED | : January 4, 2011 | |
| INVENTOR(S) | : Michael Boll et al. | |

It is certified that error appears in the above-identified patent and that said Letters Patent is hereby corrected as shown below:

In column 15, line 64, delete "ES" and insert -- HES --, therefor.

In column 19, line 12, in Claim 1, delete "hydroxyethvlstarch" and insert -- hydroxyethylstarch --, therefor.

In column 19, line 18, in Claim 2, delete "normonovolemia," and insert -- normovolemia, --, therefor.

In column 19, line 24, in Claim 2, delete "weight." and insert -- weight, --, therefor.

In column 19, line 31, in Claim 3, after "efficiency" insert -- , --.

In column 19, line 44, in Claim 4, delete "weight." and insert -- weight, --, therefor.

In column 19, line 52, in Claim 5, delete "Mw" and insert -- Mw. --, therefor

In column 19, line 63, in Claim 6, delete "weight." and insert -- weight, --, therefor In column 20, line 9, in Claim 11, delete "C2/C6" and insert -- $C_2/C_6$ --, therefor.

In column 22, line 30, in Claim 51, delete "thehydroxyethylstarch." and insert -- the hydroxyethylstarch. --, therefor.

Signed and Sealed this
Twenty-third Day of August, 2011

David J. Kappos
*Director of the United States Patent and Trademark Office*